(12) United States Patent
Nevins et al.

(10) Patent No.: US 9,265,613 B2
(45) Date of Patent: Feb. 23, 2016

(54) CEMENTLESS TIBIAL IMPLANT

(71) Applicant: Russell Nevins, Las Vegas, NV (US)

(72) Inventors: Russell Nevins, Las Vegas, NV (US); Declan Brazil, Chatswood (AU)

( * ) Notice: Subject to any disclaimer, the term of this patent is extended or adjusted under 35 U.S.C. 154(b) by 0 days.

(21) Appl. No.: 14/035,727

(22) Filed: Sep. 24, 2013

(65) Prior Publication Data
US 2014/0222156 A1 Aug. 7, 2014

Related U.S. Application Data

(60) Provisional application No. 61/705,125, filed on Sep. 24, 2012.

(51) Int. Cl.
*A61F 2/38* (2006.01)
*A61F 2/30* (2006.01)

(52) U.S. Cl.
CPC .............. *A61F 2/3886* (2013.01); *A61F 2/389* (2013.01); *A61F 2002/3069* (2013.01); *A61F 2002/30135* (2013.01); *A61F 2002/30233* (2013.01); *A61F 2002/30332* (2013.01); *A61F 2002/30387* (2013.01); *A61F 2002/30538* (2013.01); *A61F 2002/30736* (2013.01)

(58) Field of Classification Search
CPC ......... A61F 2/389; A61F 2/38; A61F 2/3886; A61F 2002/30878
USPC ................................. 623/20.21, 20.32–30.34
See application file for complete search history.

(56) References Cited

U.S. PATENT DOCUMENTS

| | | | |
|---|---|---|---|
| 4,634,444 A | 1/1987 | Noiles |
| 4,846,839 A | 7/1989 | Noiles |
| 4,888,021 A | 12/1989 | Forte et al. |
| 5,011,496 A | 4/1991 | Forte et al. |
| 5,480,445 A | 1/1996 | Burkinshaw |
| 5,658,341 A | 8/1997 | Delfosse |
| 5,782,920 A | 7/1998 | Colleran |
| 6,053,945 A | 4/2000 | O'Neil et al. |
| 6,146,424 A | 11/2000 | Gray, Jr. et al. |
| 6,214,052 B1 | 4/2001 | Burkinshaw |

(Continued)

FOREIGN PATENT DOCUMENTS

| | | |
|---|---|---|
| EP | 2347732 | 11/2011 |
| WO | WO 2009108683 | 9/2009 |

OTHER PUBLICATIONS

K.H. Widmer, B. Zurfluh, Compliant Positioning of Total Hip Components for Optimal Range of Motion, Journal of Orthopaedic Research, 2004, pp. 815-821, vol. 22, Elsever Ltd., U.S.A.

(Continued)

*Primary Examiner* — Jason-Dennis Stewart
(74) *Attorney, Agent, or Firm* — Clayton, Howarth & Cannon, P.C.

(57) ABSTRACT

A cementless orthopedic implant is disclosed. More specifically, but not necessarily entirely, a cementless tibial implant used as a component of a knee joint is disclosed. The tibial component may comprise a tibial tray and stem. The tibial component may be a monoblock design used for both primary and revision surgeries. The stem of the tibial component may comprise a plurality of protruding steps that assist in providing primary fixation and stability without the use of screws or cement. The stem of the tibial component may further comprise a first and second stepped wing portions.

32 Claims, 16 Drawing Sheets

(56) References Cited

U.S. PATENT DOCUMENTS

| | | |
|---|---|---|
| 6,575,986 B2 | 6/2003 | Overaker |
| 6,620,198 B2 | 9/2003 | Burstein et al. |
| 6,660,039 B1 | 12/2003 | Evans et al. |
| 7,153,326 B1 | 12/2006 | Metzger |
| 7,291,174 B2 | 11/2007 | German et al. |
| 7,309,355 B2 | 12/2007 | Donnelly et al. |
| 7,357,817 B2 | 4/2008 | D'Alessio, II |
| 7,422,605 B2 | 9/2008 | Burstein et al. |
| 7,988,736 B2 | 8/2011 | May et al. |
| 8,012,217 B2 | 9/2011 | Strzepa et al. |
| 8,043,375 B2 | 10/2011 | Strzepa et al. |
| 8,092,530 B2 | 1/2012 | Strzepa et al. |
| 8,092,546 B2 | 1/2012 | Coon et al. |
| 8,382,849 B2 | 2/2013 | Thomas |
| 2003/0014122 A1* | 1/2003 | Whiteside ............ 623/20.32 |
| 2007/0010890 A1 | 1/2007 | Collazo |
| 2008/0021566 A1 | 1/2008 | Peters et al. |
| 2010/0057212 A1 | 3/2010 | Thomas |
| 2010/0114323 A1* | 5/2010 | Deruntz et al. ........... 623/20.21 |
| 2010/0161055 A1 | 6/2010 | Donnelly et al. |
| 2011/0178606 A1 | 7/2011 | Deffenbaugh et al. |
| 2013/0166037 A1 | 6/2013 | Goodfellow et al. |

OTHER PUBLICATIONS

DePuy International Ltd, Knee Revision—Product Portfolio, Mar. 2009, England.

* cited by examiner

A-A

B-B

CEMENTLESS TIBIAL IMPLANT

CROSS-REFERENCE TO RELATED APPLICATIONS

This application claims the benefit of U.S. Provisional Application No. 61/705,125, filed Sep. 24, 2012, which is hereby incorporated by reference herein in its entirety, including but not limited to those portions that specifically appear hereinafter, the incorporation by reference being made with the following exception: In the event that any portion of the above-referenced provisional application is inconsistent with this application, this application supercedes said above-referenced provisional application.

STATEMENT REGARDING FEDERALLY SPONSORED RESEARCH OR DEVELOPMENT

Not Applicable.

BACKGROUND

The disclosure relates generally to orthopedic implants, and more particularly, but not necessarily entirely, to a cementless tibial implant and component of a knee joint.

In total knee arthroplasty, the knee joint is replaced with an artificial knee implant. The knee implant traditionally includes a femoral component and a tibial component. It is common practice to ream a portion of the bone (the distal end of the femur and the proximal portion of the tibia) to provide a channel to receive a stem of either the femoral component or the tibial component. A first knee replacement is referred to as a primary surgery. Fixation of the implant to the bone (femur or tibia) in a primary surgery may be achieved through cementing the implant to the bone or biologic fixation (non-cemented techniques) or otherwise.

In some cases, over time, implants may fail for one reason or another. For example, wear, infection, improper loading of the bone followed by loosening of the implant in the bone are reasons for implant failure. In such cases, a revision surgery may be required to properly fix the implant to the bone.

Despite the advantages of modern knee replacement systems, improvements are still being sought. The disclosure relates to a cementless tibial component that may be used in a primary surgery or in a revision surgery. The disclosure minimizes, and in some aspects eliminates, the failures encountered in modern tibial components by utilizing the methods and structural features described herein.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out herein.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
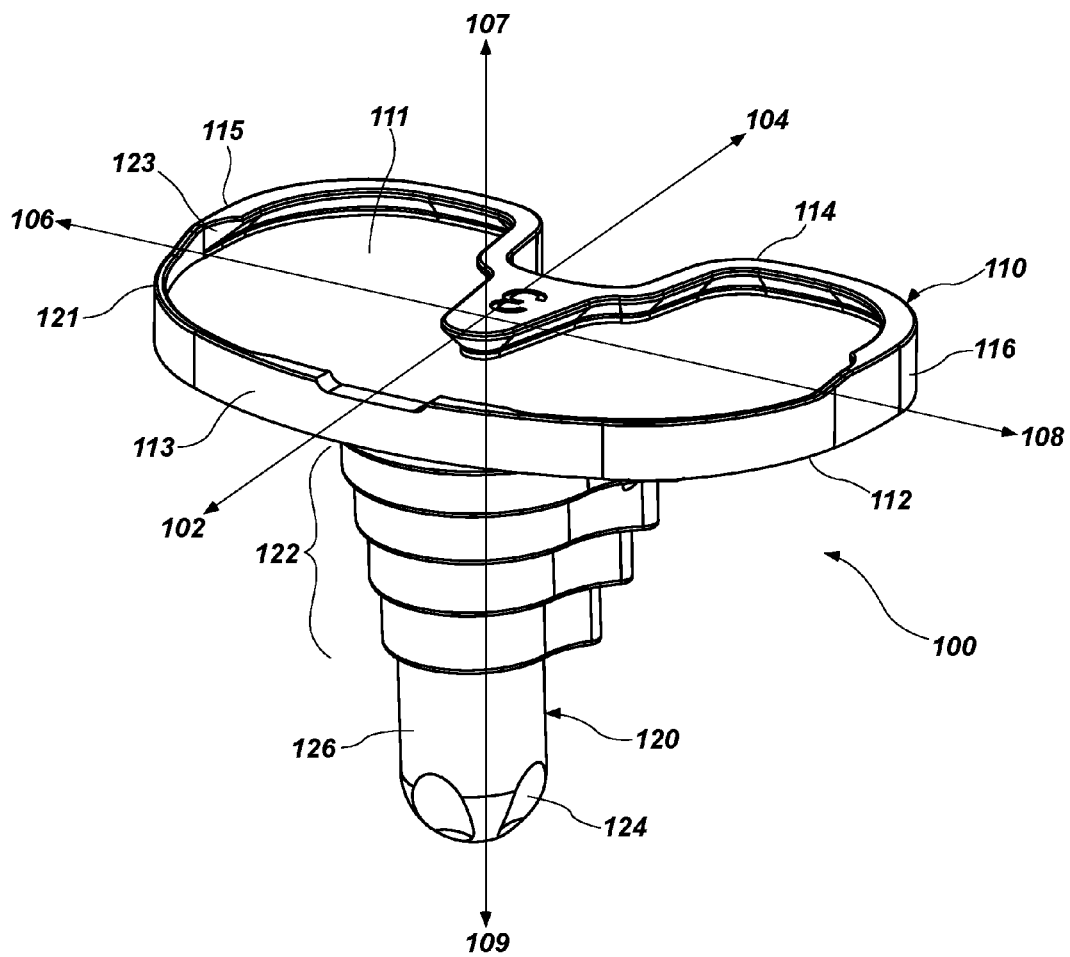
FIG. 1 is a perspective view of a cementless tibial component made in accordance with the principles of the disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure.

Before the structures, systems and associated methods relating to the cementless tibial component and implant are disclosed and described, it is to be understood that this disclosure is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the disclosure will be limited only by the claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the term "proximal" shall refer broadly to the concept of a nearest portion. For example, the tibial component of a knee implant is implanted into the proximal-most portion of the tibial bone because it is the portion of the bone that is nearest the trunk of the person's body.

As used herein, the term "distal" shall generally refer to the opposite of proximal, and thus to the concept of a further portion, or a furthest portion, depending upon the context. For example, the femoral component of a knee implant is implanted into the distal-most portion of the femoral bone because it is implanted into the portion of the bone that is farthest away from the person's body.

As used herein, the phrase "in an at least partially proximal-to-distal direction" shall refer generally to a two-dimensional concept of direction in which the "proximal-to-distal" direction defines one direction or dimension. An item that extends in a non-parallel direction with respect to the "proximal-to-distal" direction, that is, at a non-straight angle thereto, thereby involves two components of direction, one of which is in the "proximal-to-distal" direction and the other being in a direction orthogonal to the "proximal-to-distal" direction.

Referring now to FIG. 1, a tibial implant or component 100 made in accordance with the principles of the disclosure is illustrated. It will be appreciated that the anterior side of the tibial implant is generally illustrated by 102, the posterior side generally by 104, the medial side generally by 106, the lateral side generally by 108, the superior side 107, and the inferior side 109. It will further be appreciated that, as used herein, the term "proximal" refers to the direction or part closest to the femur and the term "distal" refers to the direction or part closest to the foot.

In an embodiment, the tibial implant 100 may comprise a tibial tray 110 and a tibial stem 120. In particular, the tibial tray 110 may comprise an upper (superior) surface 111 and a lower (inferior) surface 112. The stem 120 may extend in the superior-to-inferior direction from the lower surface 112 of the tibial tray 110. The stem 120 may be configured and adapted to be installed into a cavity formed in a cut surface exposed by resecting the head of the tibia (not shown). In addition, the tibial tray 110 may also comprise an anterior side 113, a posterior side 114, a medial side 115, and a lateral side 116 as known to those having ordinary skill.

Extending upwardly from the perimeter of the upper surface 111 may be a wall 121. The wall 121 and upper surface 111 may define a seat for receiving a tibial bearing insert. The wall 121, along the posterior portion of the upper surface 111, may include a tapered, inwardly extending locking lip 123 for securing a tibial bearing insert. In an embodiment, the upper surface 111 of the tibial implant 100 may be devoid of any cavities for receiving a stem of a tibial bearing insert.

Figure 8:
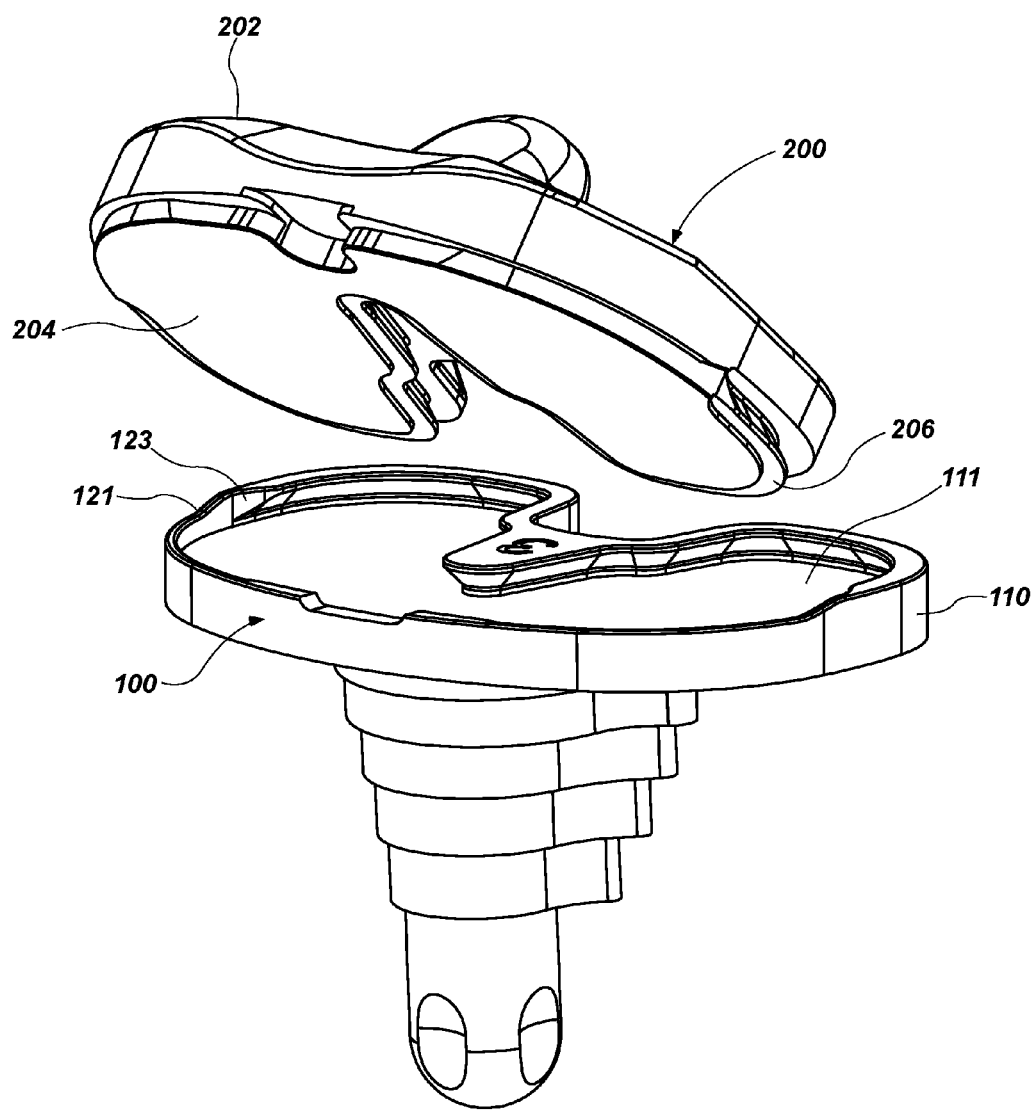
FIG. 8 is an exploded, perspective view of a cementless tibial component and tibial bearing insert made in accordance with the principles of the disclosure.
Figure 9:
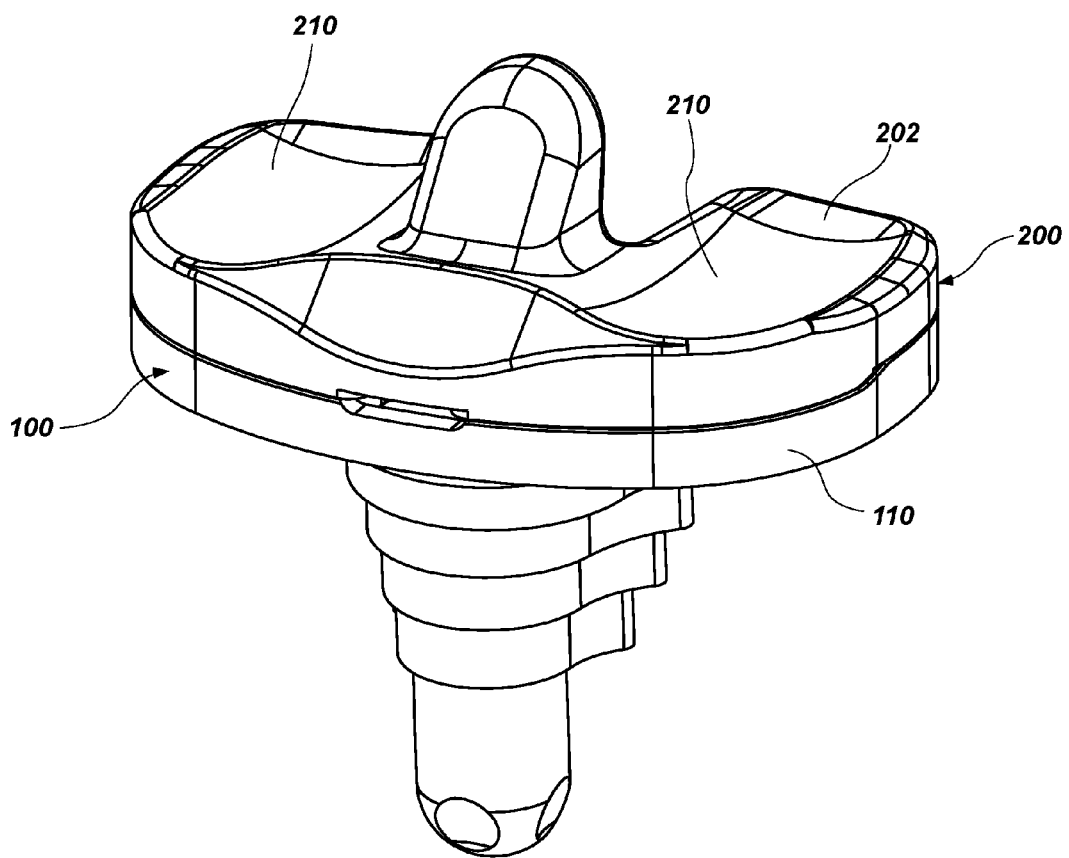
FIG. 9 is an unexploded, perspective view of a cementless tibial component and tibial bearing insert made in accordance with the principles of the disclosure.

Referring now to FIGS. 8 and 9, the superior surface 111 of the tibial tray 110 may be configured and adapted to receive a tibial bearing insert 200. In particular, a tibial bearing insert 200 may comprise a superior surface 202 and an inferior surface 204. The inferior surface 204 may be adapted to engage the superior surface 111 of the tibial tray 110. In this regard, extending outwardly from a perimeter of the inferior surface 204 may be a locking lip 206. In an embodiment, the locking lip 206 may be tapered. The locking lip 206 may be configured and adapted to matingly engage the locking lip 123 of the superior surface 111 of the tibial tray 110 such that the insert 200 is locked to the tibial tray 110. When locked, the wall 121 and locking lips 206 and 123 may prevent the tibial bearing insert 200 from rotating.

In an embodiment, the superior surface 202 of the tibial bearing insert 200 may have one or more condylar regions 210 that are adapted to receive, and articulate with, complementary condyles of a femoral implant (not shown) as known to those having ordinary skill in the art.

In an embodiment, the tibial stem 120 may comprise a plurality of protruding steps or terraces 122, a plurality of concave portions 124 and a shaft 126. The plurality of protruding steps 122 may extend outwardly from the shaft 126. In an embodiment, the tibial stem 120 may be formed in a unitary manner with respect to the tibial tray 110. The tibial stem 120 may extend in a distal direction (superior-to-inferior) from the lower surface 112 of the tibial tray 110. It will be appreciated that the tibial implant 100 may be considered a monoblock tibial implant because the tibial tray 110 and the tibial stem 120 may be manufactured as a unitary or single structure without interchangeable or modular parts. However, it will be appreciated that additional structures may be added onto the monoblock portion of the tibial implant 100. For example, other components may be added to the shaft 126, but are not interchangeable with shaft 126, of the tibial stem 120.

Figure 4:
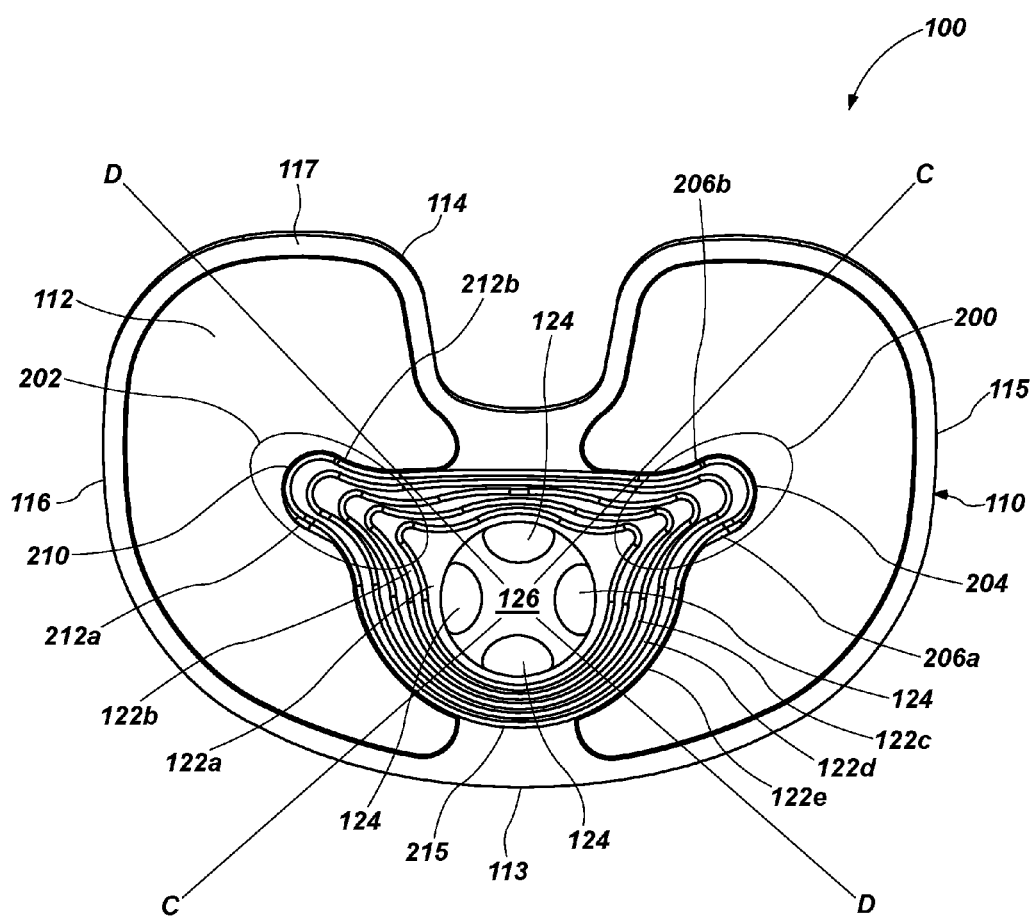
FIG. 4 is a bottom view of a cementless tibial component made in accordance with the principles of the disclosure.

Referring now to FIG. 4, and particularly to the plurality of protruding steps 122 illustrated therein, it will be appreciated that each of the protruding steps 122 may be progressively and successively wider in the medial-lateral direction than the protruding step 122 immediately beneath it (steps 122 are individually labeled 122a-122e). As illustrated, beginning with the distal most protruding step 122a and moving upward toward the proximal most protruding step 122e, each of the protruding steps 122a-122e gets progressively and successively wider in the medial-lateral direction than the step immediately below it. In an embodiment, one or more of the plurality of steps 122 may include a porous surface or other surface treatment to encourage bone growth. In an embodiment, all of the steps 122 except one may include a porous surface or other surface treatment to encourage bone growth. In an embodiment, the steps 122b-122e may include a porous surface while the step 122a and the shaft 126 does not. In an embodiment, the plurality of steps 122 may include two, three, four, five, six or more steps. In an embodiment, the inferior surface 112 may include a porous surface or other surface treatment to encourage bone growth.

Figure 2:
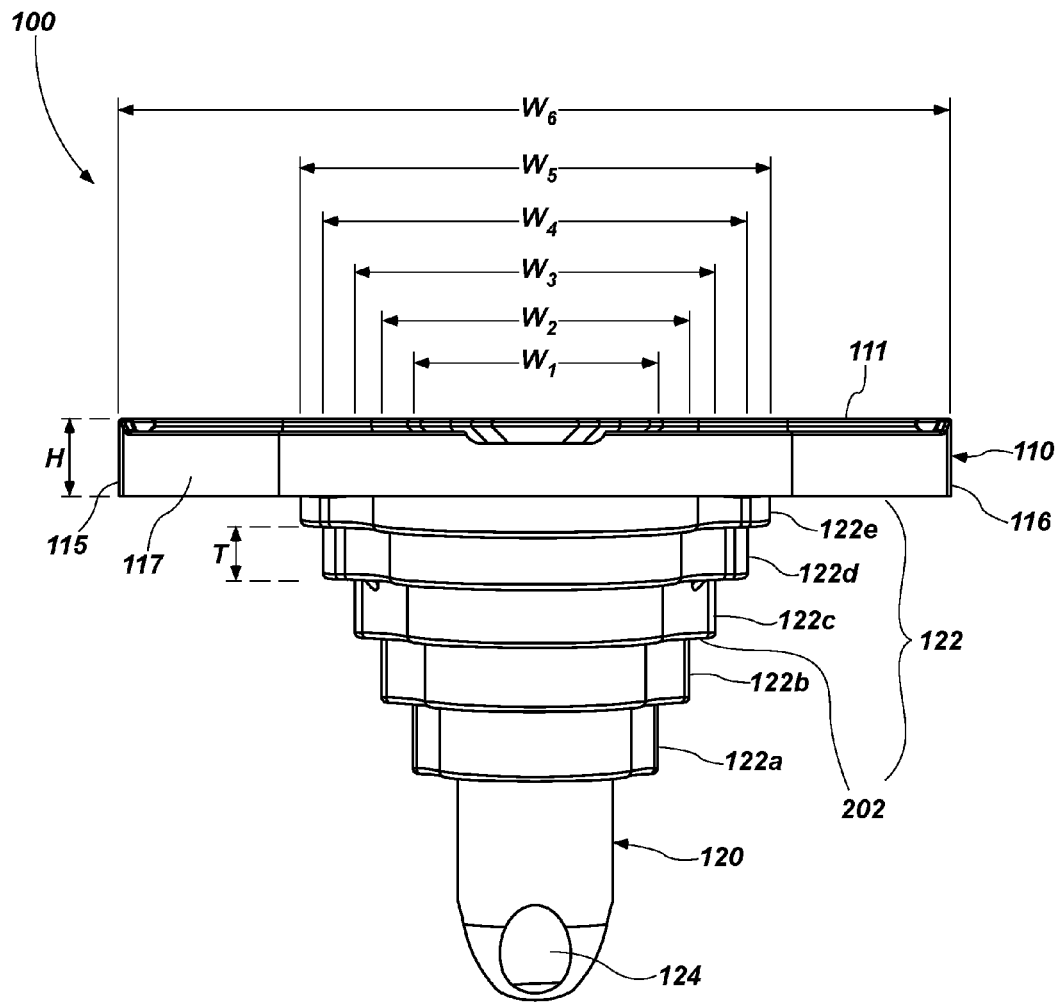
FIG. 2 is a front view of a cementless tibial component made in accordance with the principles of the disclosure.

Referring now to FIGS. 2 and 4, the tibial stem 120 may further comprise a medial wing 200 and a lateral wing 202. In particular, the medial wing 200 and the lateral wing 202 may extend from the lower surface 112 along the sides of the stem 120. The medial wing 200 and the lateral wing 202 may extend from the lower surface 112 along the steps 122. It will be appreciated that the steps 122, 122a-122b, may extend into the medial wing 200 and the lateral wing 202 such that the medial wing 200 and the lateral wing 202 may be stepped or terraced.

Each of the steps 122 may include a first localized convex portion or lobe portion 204 that defines the medial wing 200. The lobe portion 204 of each of the steps 122 may be interposed between concave portions 206a and 206b. In this regard, the concave portions 206a and 206b may define a neck for the lobe portion 204. Further, each of the steps 122 may include a second localized convex or lobe portion 210 that defines the lateral wing 202. The lobe portion 210 of each of the steps 122 may be interposed between concave portions 212a and 212b. In this regard, the concave portions 212a and 212b may define a neck for the lobe portion 210. In an embodiment, the stem 120 may only include a single wing, either on the medial or lateral side. In an embodiment, each of the steps 122 may include a third localized convex portion or lobe portion 215. The lobe portion 215 of each of the steps 122 may be interposed between concave portions 212a and 206a. The concave portions 212a and 206a may define a neck for the lobe portion 215. It will be appreciated the lobe portions 204 may define medial lobes, the lobe portions 210 may define lateral lobes, and the lobe portions 215 may define anterior lobes of the plurality of steps 122. In an embodiment, at least two of the steps 122 may comprise one or more lobe portions. In an embodiment, a majority of the steps 122 may comprise one or more lobe portions. In an embodiment, all of the plurality of steps 122 may comprise one or more lobe portions.

Referring now to just FIG. 2, it will be appreciated that the tibial tray 110 may comprise a tray width ($W_6$ in FIG. 2) that may be defined between the medial side 115 and the lateral side 116 of the tibial tray 110. Additionally, each of the plurality of protruding steps 122 may comprise a step width ($W_1$ through $W_5$ in FIG. 2) that may be defined as a distance that is less than, and formed between, the medial side 115 and the lateral side 116 of the tibial tray 110.

A ratio may exist between the tray width $W_6$ and the step width $W_1$ through $W_5$, wherein the ratio may be between about 1:0.75 and about 1:0.2. For example, there may be a ratio of the tibial tray 110 with respect to the distal most protruding step 122a, such that the ratio of the tray width $W_6$ to the step width $W_1$ may be about 1:0.2 to about 1:0.3. By way of further example, there may be a ratio of the tibial tray 110 with respect to the next successive protruding step 122b, such that the ratio of the tray width $W_6$ to the step width $W_2$ may be about 1:0.3 to about 1:0.4. By way of further example, there may be a ratio of the tibial tray 110 with respect to the next successive protruding step 122c, such that the ratio of the tray width $W_6$ to the step width $W_3$ may be about 1:0.4 to about 1:0.5. By way of further example, there may be a ratio of the tibial tray 110 with respect to the next successive protruding step 122d, such that the ratio of the tray width $W_6$ to the step width $W_4$ may be about 1:0.5 to about 1:0.6. By way of further example, there may be a ratio of the tibial tray 110 with respect to the next successive protruding step 122e, such that the ratio of the tray width $W_6$ to the step width $W_5$ may be about 1:0.6 to about 1:0.75. As demonstrated by the above examples, the stem width $W_1$ through $W_5$ in FIG. 2 of each successive protruding step 122, as measured from the distal end of the stem 120 to the proximal end of the stem 120, may increase.

In an embodiment, the ratio between the tray width $W_6$ and the step width $W_1$ of a distal most protruding step 122 may be between a range of about 1:0.25 to about 1:0.35. In an embodiment, a ratio between the tray width $W_6$ and the step width $W_5$ of a proximal most step may be between a range of about 1:0.65 to about 1:0.55.

Continuing to refer to FIG. 2, each of the plurality of protruding steps 122 may comprise a thickness T defined as a distance of the individual protruding step that runs in the proximal to distal direction as illustrated best in FIG. 2. The tibial tray 110 may comprise a sidewall 117 that defines a perimeter of the top surface 111 of the tibial tray 110. The sidewall 117 comprises a height H as illustrated best in FIG. 2. A ratio may exist between the thickness T of at least one of the plurality of protruding steps 122 with respect to the height H of the sidewall 117 of the tibial tray 110, where the ratio may be between a range of about 0.5:1 to about 1:1.

Figure 3:
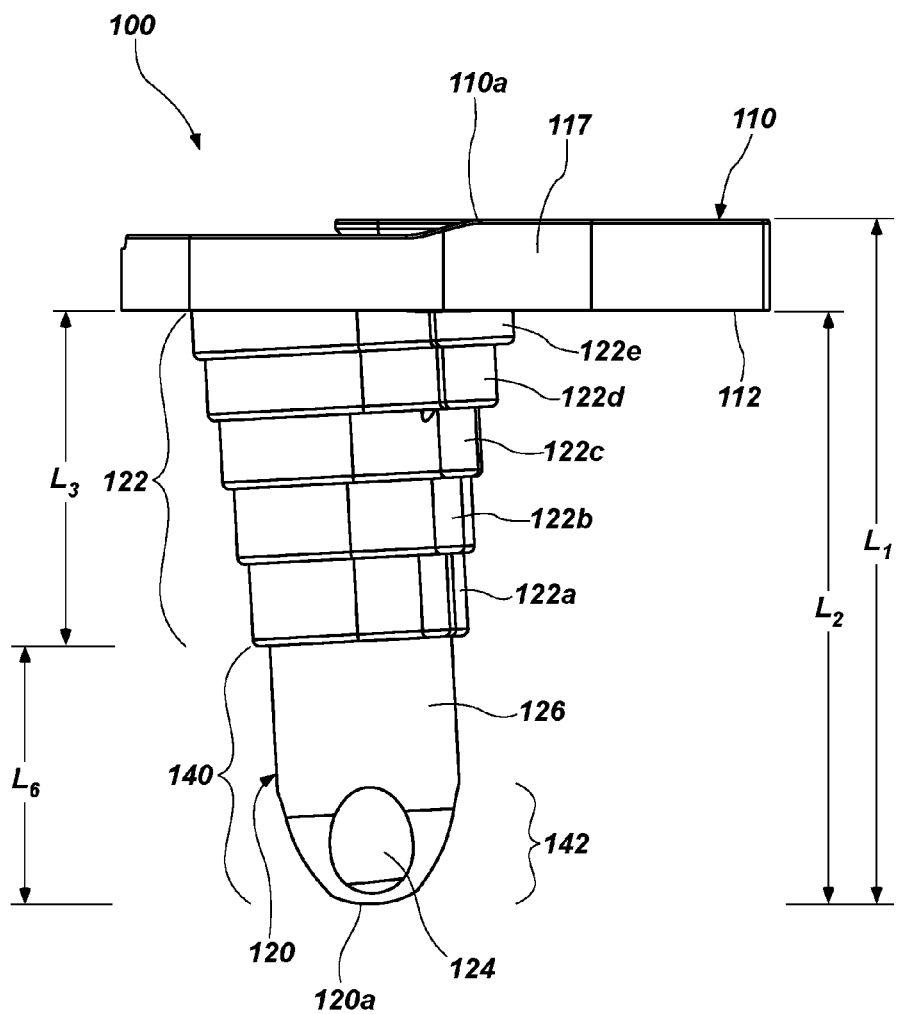
FIG. 3 is a side view of a cementless tibial component made in accordance with the principles of the disclosure.
Figure 6:
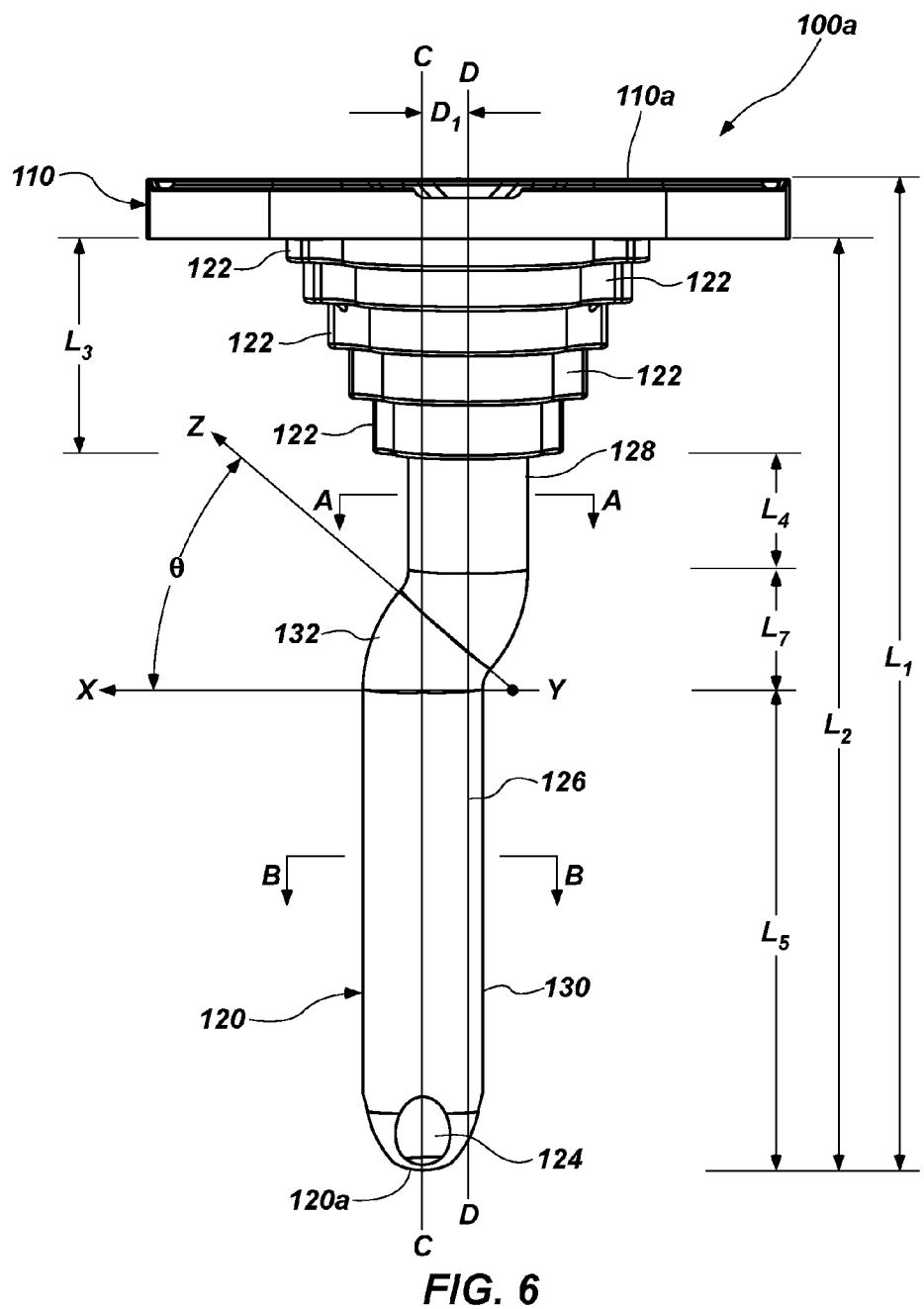
FIG. 6 is a front view of an embodiment of a cementless tibial component made in accordance with the principles of the disclosure.

Referring now to FIGS. 3 and 6, the tibial implant 100 may comprise a total length $L_1$ of the entire component that is measured from a terminal end 110a of the tibial tray 110, i.e., the proximal most terminal end of the tibial tray 110, on one end and a terminal end 120a of the tibial stem 120 at the other end. The tibial stem 120 may comprise a stem length $L_2$ that is measured from the lower surface 112 of the tibial tray 110 to the terminal end 120a of the tibial stem 120. A ratio may exist between the total length $L_1$ of the tibial implant 100 to the stem length $L_2$ of the tibial stem 120 that may be between a range of about 1:0.75 to about 1:0.95. Further, the tibial stem 120 may comprise a stem length $L_6$ that is measured from a distal most terminal end of the protruding step 122a, which is positioned within the plurality of protruding steps 122 as the distal most protruding step 122a, to the terminal end 120a of the tibial stem 120. A ratio may exist between the total length $L_1$ of the tibial implant 100 to the stem length $L_6$ of the tibial stem 120 that may be between a range of about 1:0.30 to about 1:0.45, and more particularly between a range of about 1:0.35 to about 1:0.40.

Additionally, the plurality of protruding steps 122 may be formed anywhere between the lower surface 112 of the tibial tray 110 and a distal end 120a of the tibial stem 120. The plurality of protruding steps 122 may comprise a total length $L_3$ that is defined by a distal most terminal end of the protruding step 122a, which is positioned within the group as the distal most protruding step 122, and a proximal most terminal end of the protruding step 122e, which is positioned within the group as the proximal most protruding step 122. A ratio may exist between the total length $L_1$ of the tibial implant 100 to the length $L_3$ of the plurality of protruding steps 122 that may be between a range of about 1:0.15 to about 1:0.55.

Referring specifically to FIG. 6, the tibial implant 100a illustrated may be used as a primary implant and may also be used as a revision implant. The ratio between the total length $L_1$ of the tibial implant 100 to the length $L_3$ of the plurality of protruding steps 122 illustrated in FIG. 6 may be between a range of about 1:0.15 to about 1:0.20. The ratio difference (compared to the implant of FIG. 3) is due to the addition of a longer tibial shaft 126.

Referring specifically to FIG. 3, the tibial implant 100 may be used as a primary implant and may also be used as a revision implant. The ratio between the total length $L_1$ of the tibial implant 100 to the length $L_3$ of the plurality of protruding steps 122 illustrated in FIG. 3 may be between a range of about 1:0.45 to about 1:0.55. In this case, the ratio difference (compared to the implant of FIG. 6) is due to the shorter tibial shaft 126.

Figure 5:
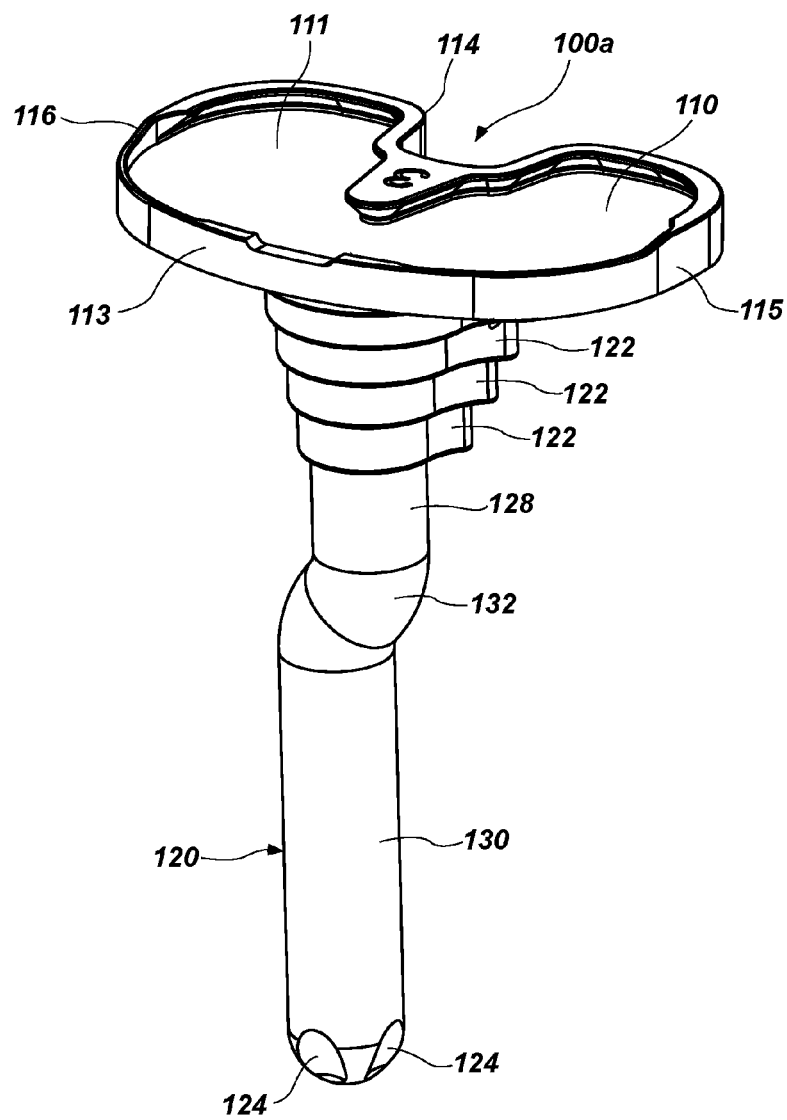
FIG. 5 is a perspective view of an embodiment of a cementless tibial component made in accordance with the principles of the disclosure.
Figure 6A:
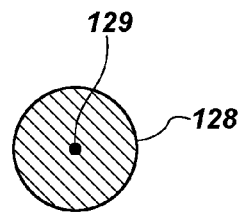
FIG. 6A is a transverse cross-sectional view taken along section A-A of FIG. 6.
Figure 6B:
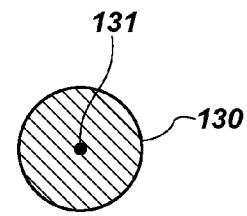
FIG. 6B is a transverse cross-sectional view taken along section B-B of FIG. 6.
Figure 7:
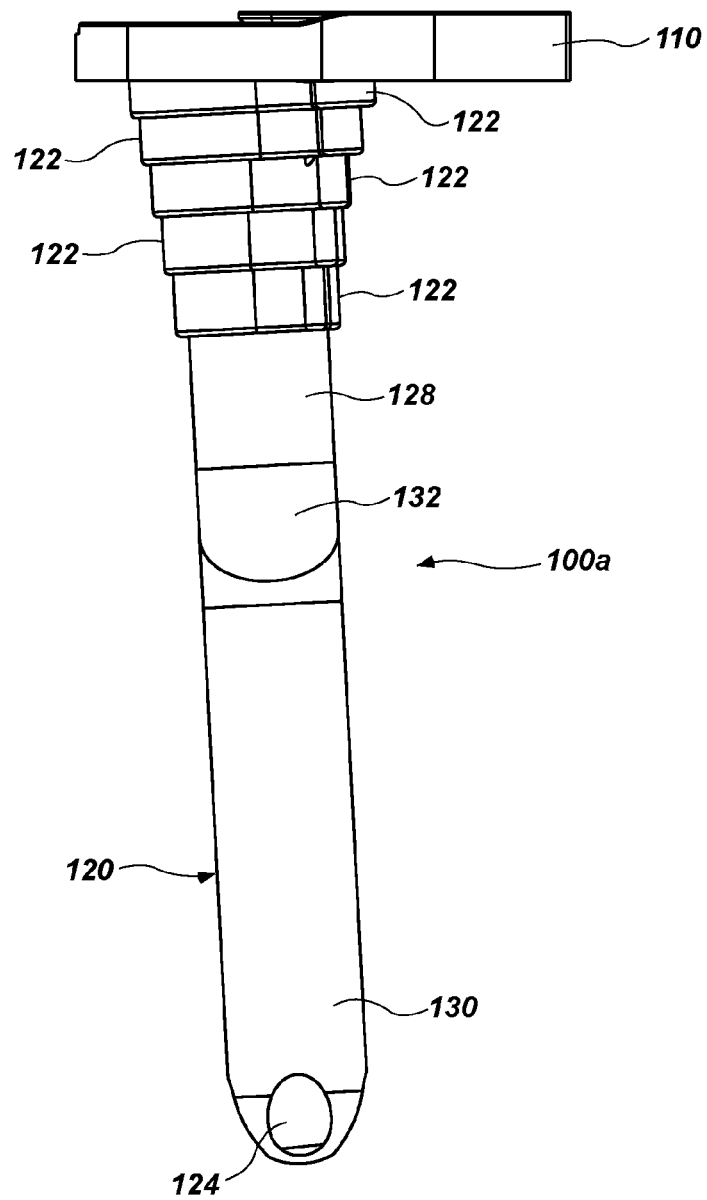
FIG. 7 is a side view of an embodiment of a cementless tibial component made in accordance with the principles of the disclosure.

Referring now to FIGS. 5-7, the tibial implant 100a may be used as a primary implant and may also be used as a revision implant. The tibial stem 120 may include one or more shafts 126. The tibial stem 120 illustrated may comprise a proximal shaft 128, a distal shaft 130 and a joint 132 formed between the proximal shaft and the distal shaft that joins the two shafts together. The proximal shaft 128 may comprise a transverse cross-section comprising a center point 129 (illustrated best in FIG. 6A and Section A-A). The distal shaft 130 may comprise a transverse cross-section comprising a center point 131 (illustrated best in FIG. 6B and Section B-B), wherein the center point 129 of the proximal shaft 128 may be offset and may be non-linear with respect to the center point 131 of the distal shaft 130 as illustrated in FIGS. 5-7 to create a dogleg. The dogleg offset may be defined by the distance $D_1$ between the center point 129 of the proximal shaft 128 and the center point 131 of the distal shaft 130. A ratio may exist between a length of the joint 132, which may be defined as $L_7$, and the distance $D_1$ between center points 129 and 131, where the ratio may be about 1:0.2 to about 1:0.6, or about 1:0.3 to about 1:0.5, or about 1:0.4.

Further, in a sagittal or coronal cross-section of the implant 100, the joint 132 may comprise an angle θ formed by the intersection of (1) an imaginary line (XY), where Y is the vertex, that is orthogonal to a longitudinal axis (C-C) that runs through the center point 131 of the distal shaft 130 and that is formed at the proximal most portion of the distal stem 130; and (2) an imaginary line (YZ) that passes through a location where the outer surface of the joint 132 transitions from a vertical line having an infinite slope to a curved surface having a positive slope, as illustrated best in FIG. 6. The angle θ may be between a range of about thirty degrees to about sixty degrees, or more particularly about forty-five degrees.

As noted above, the tibial implant 100 may comprise an overall or total length $L_1$. The proximal shaft 128 may comprise an overall or total length, and may further comprise a length $L_4$ that is measured as the difference between the length $L_3$ of the plurality of protruding steps 122 and the total length of the proximal shaft 128. The distal shaft 130 of the tibial stem 120 may comprise a stem length $L_5$ that is measured from a terminal end of the joint 132 proximally to the terminal, distal end 120a of the distal shaft 130 distally. A ratio may exist between the total length $L_1$ of the tibial implant 100 to the stem length $L_5$ of the distal shaft 130 that may be between a range of about 1:0.4 to about 1:0.6. As illustrated best by FIG. 6, the joint 132 formed between the proximal shaft 128 and the distal shaft 130 may comprise a one-hundred and eighty degree transition from a positive slope to a negative slope, such that the joint transition creates the offset between the proximal shaft 128 and the distal shaft 130.

In an embodiment, the joint 132 may be a modular joint, such that the proximal shaft 128 may move relative to the distal shaft 130. In an embodiment, the modular joint itself may rotate and swivel about an axis, thereby allowing the proximal shaft 128 to move with respect to the distal shaft 130. In an embodiment, the joint 132 may be an adaptor that connects to the proximal shaft 128 at one end and to the distal shaft 130 at the other end. The adaptor joint may provide the offset to allow a surgeon to locate the tibial implant 100 into varying anatomies. In an embodiment, the joint 132 may be a monoblock joint, such that the proximal shaft 128 may remain static with respect to the distal shaft 130. It will be appreciated that in all embodiments of the joint 132, the joint 132 provides an offset to account for anatomical variations and differences in the tibial bone. Further, it will be appreciated that the modular joint and/or the adaptor may be coupled, connected or attached to the proximal shaft 128 and/or the distal shaft 130 via any conventional connection or coupling device that is known in the mechanical arts, such as a threaded connection, a press-fit connection, a key and keyway or other mechanical coupling or connection.

Referring now to FIGS. 1-7, and particularly to FIGS. 3 and 4, the tibial stem 120 may comprise a plurality of concave portions 124 located on a distal most one-third 142 of the tibial stem 120. Each of the plurality of concave portions 124 may lie in a quadrant defined by intersecting two imaginary planes (represented by lines C-C and D-D) perpendicularly to each other to create individual quadrants (illustrated best in FIG. 4). Each of the concave portions 124 may comprise about ten percent to about thirty percent of total planar section of a portion 140 of the tibial stem 120 that is free from the protruding steps 122. It will be appreciated that each of the concave portions 124 may comprise about forty percent to about seventy percent of a perimeter section of the distal most one-third 142 of the tibial stem 120.

Figure 10:
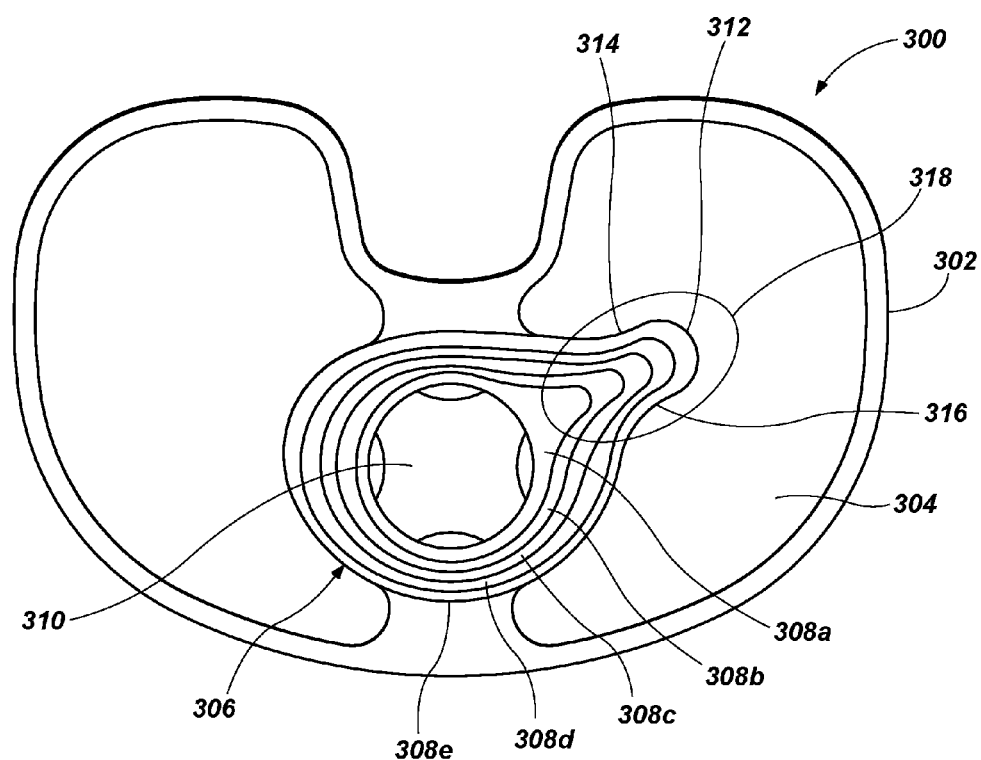
FIG. 10 is a bottom view of a tibial component with a stepped stem made in accordance with the principles of the disclosure.
Figure 11:
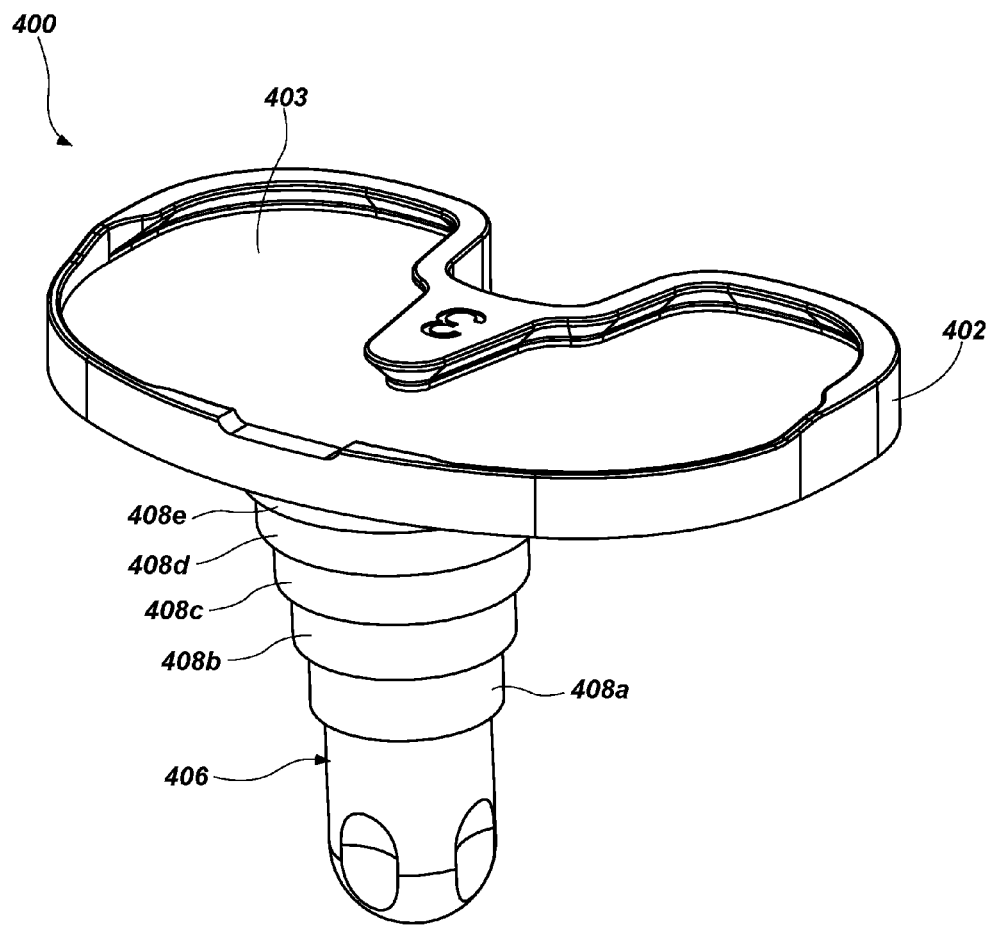
FIG. 11 is a perspective view of a cementless tibial component made in accordance with the principles of the disclosure.
Figure 12:
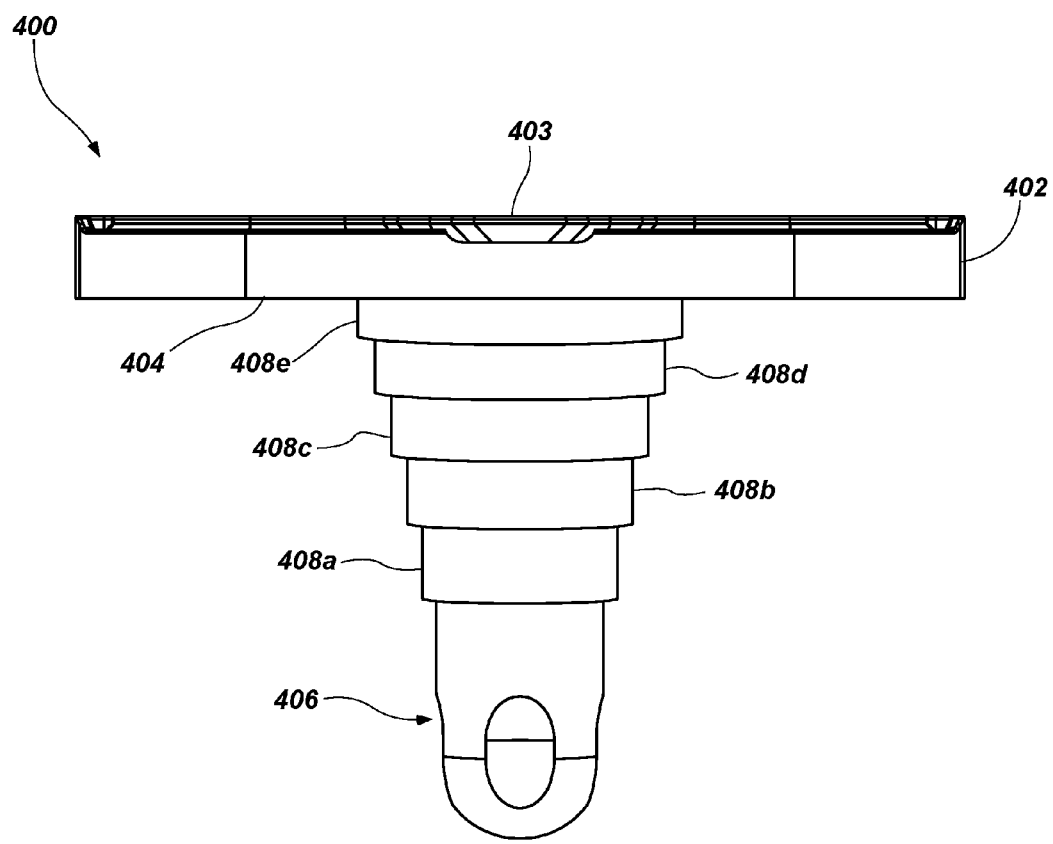
FIG. 12 is a front view of the cementless tibial component shown in FIG. 11.
Figure 13:
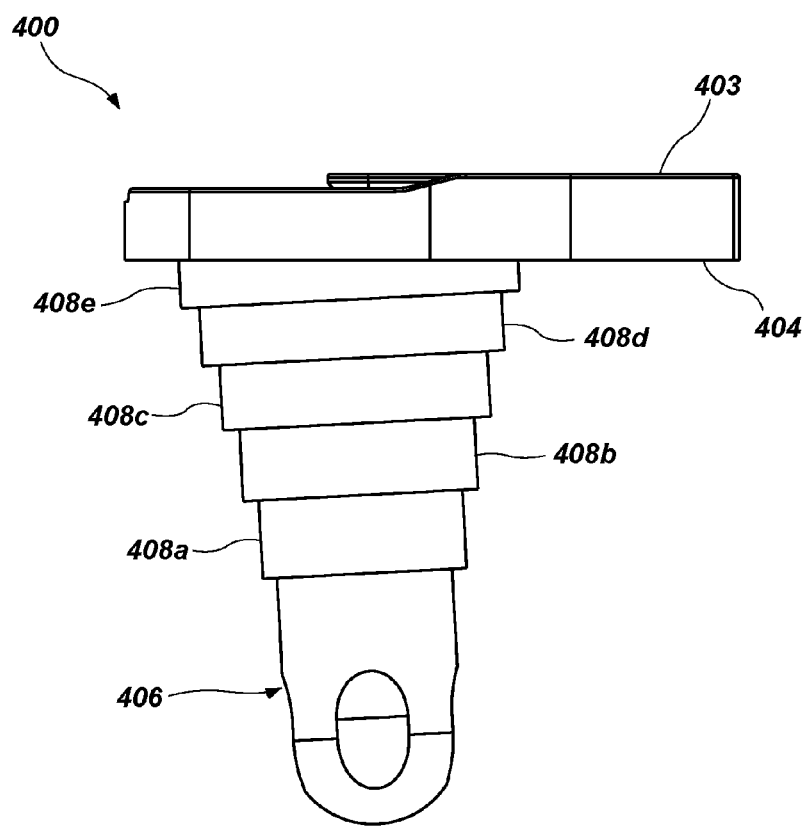
FIG. 13 is a side view of the cementless tibial component shown in FIG. 11.
Figure 14:
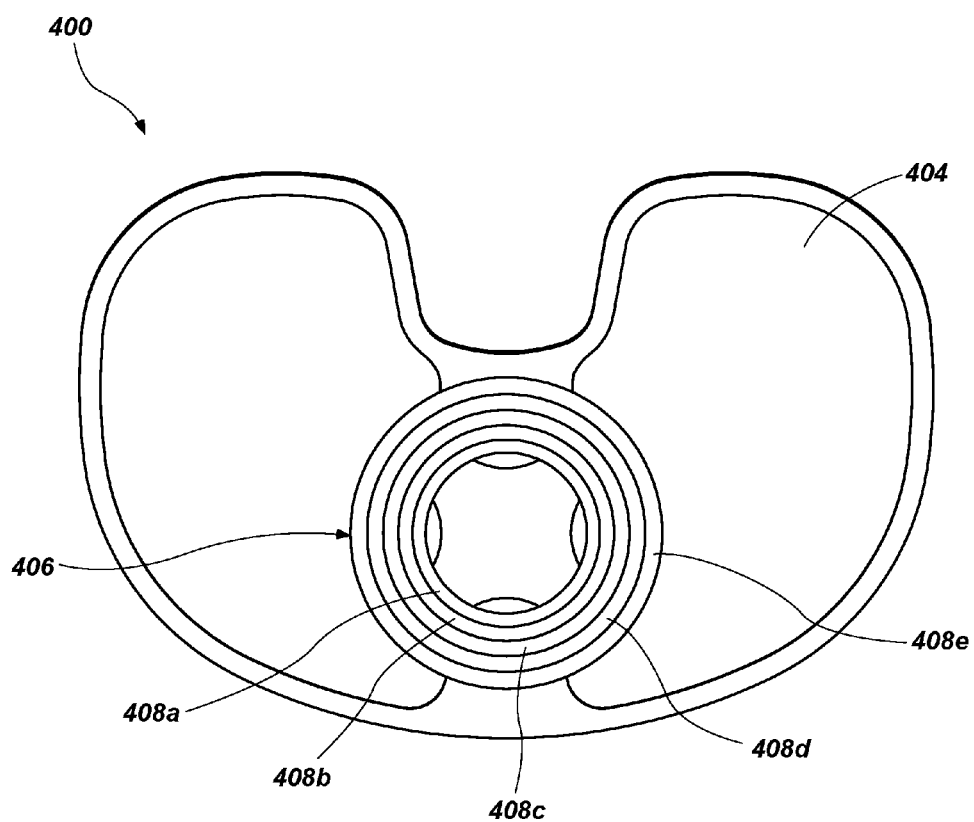
FIG. 14 is a bottom view of the cementless tibial component shown in FIG. 11.

Referring now to FIG. 10, there is depicted a tibial component or implant 300 according to an embodiment of the present disclosure. The implant 300 may be similar to the implant 100, except for the differences noted specifically herein. The implant 300 may include a tibial tray 302 having a superior surface (not visible) and an inferior surface 304. Extending downwardly from the inferior surface 304 may be a stem 306. The stem 306 may comprise a plurality of steps 308a-308e, and generally referred to herein by reference numeral 308. It will be appreciated that each of the protruding steps 308 may be progressively and successively wider in the medial-lateral direction than the protruding one of the steps 308 immediately beneath it. As illustrated, beginning with the distal most protruding step 308a and moving upward toward the proximal most protruding step 308e, each of the protruding steps 308a-308e gets progressively and successively wider in the medial-lateral direction than the step immediately below it.

As can be observed, each of the steps 308 include a local convex portion or lobe portion 312. Each of the lobe portions 312 of the steps 308 may be interposed between a first concave portion 312 and a second concave portion 314. The lobe portions 312 may form a wing 318 of the stem 306. In an embodiment, the steps 308, and stem 306, may be eccentric due to the lobe portions 312. It will be appreciated that the stem 306 may comprise a single, eccentric wing portion 318.

Referring now to FIGS. 11-14, there is depicted a tibial component or implant 400 according to an embodiment of the present disclosure. The implant 400 may be similar to the implant 100, except for the differences noted specifically herein. The implant 400 may include a tibial tray 402 having a superior surface 403 and an inferior surface 404. Extending downwardly from the inferior surface 404 may be a stem 406. The stem 406 may comprise a plurality of steps 408a-408e, and generally referred to herein by reference numeral 408. It will be appreciated that each of the protruding steps 408 may be progressively and successively wider in the medial-lateral direction than the protruding one of the steps 408 immediately beneath it. As illustrated, beginning with the distal most protruding step 408a and moving upward toward the proximal most protruding step 408e, each of the protruding steps 408a-408e gets progressively and successively wider in the medial-lateral direction than the step immediately below it. As perhaps best viewed in FIG. 14, steps 408a-408e may have a circular cross-section.

Figure 15:
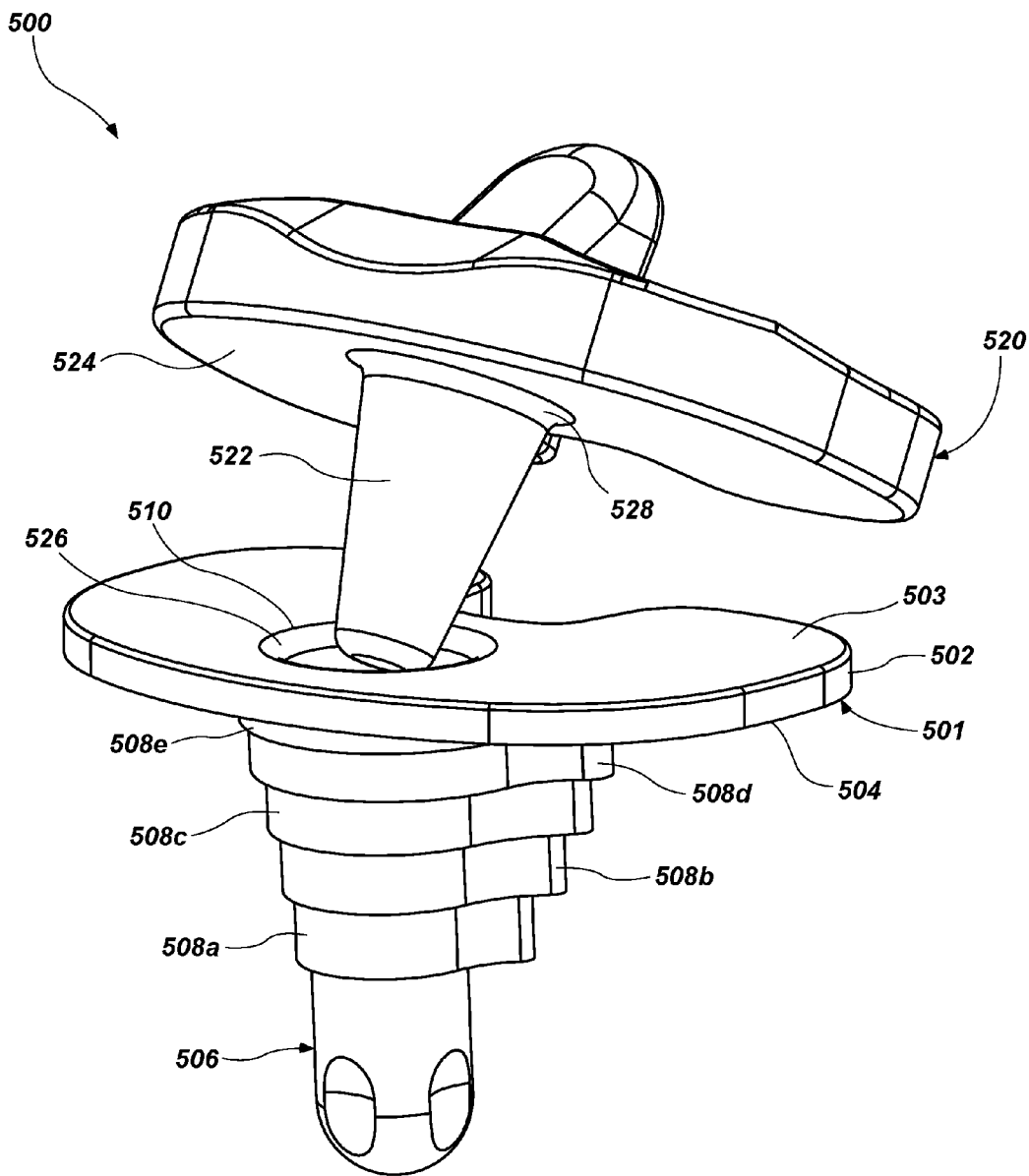
FIG. 15 is an exploded, perspective view of a cementless tibial component and tibial bearing insert made in accordance with the principles of the disclosure.

Referring now to FIG. 15, there is depicted a mobile bearing knee prosthesis 500 according to an embodiment of the present disclosure. The prosthesis 500 may include a tibial component or implant 501 and a tibial bearing insert 520. In an embodiment, the tibial component 501 may be similar to the implant 100, except for the differences noted specifically herein. The implant 501 may include a tibial tray 502 having a superior surface 503 and an inferior surface 504.

Extending downwardly from the inferior surface 504 may be a stem 506. The stem 506 may comprise a plurality of steps 508a-508e, and generally referred to herein by reference numeral 508. It will be appreciated that each of the protruding steps 508 may be progressively and successively wider in the medial-lateral direction than the protruding one of the steps 508 immediately beneath it. As illustrated, beginning with the distal most protruding step 508a and moving upward toward the proximal most protruding step 508e, each of the protruding steps 508a-508e gets progressively and successively wider in the medial-lateral direction than the step immediately below it. In an embodiment, the steps 508 may include a localized convex portion or lobe portion similar to the steps 308 shown in FIG. 10. In an embodiment, the steps 508 may include two localized convex portions or lobe portions similar to the steps 122 shown in FIG. 4.

Figure 16:
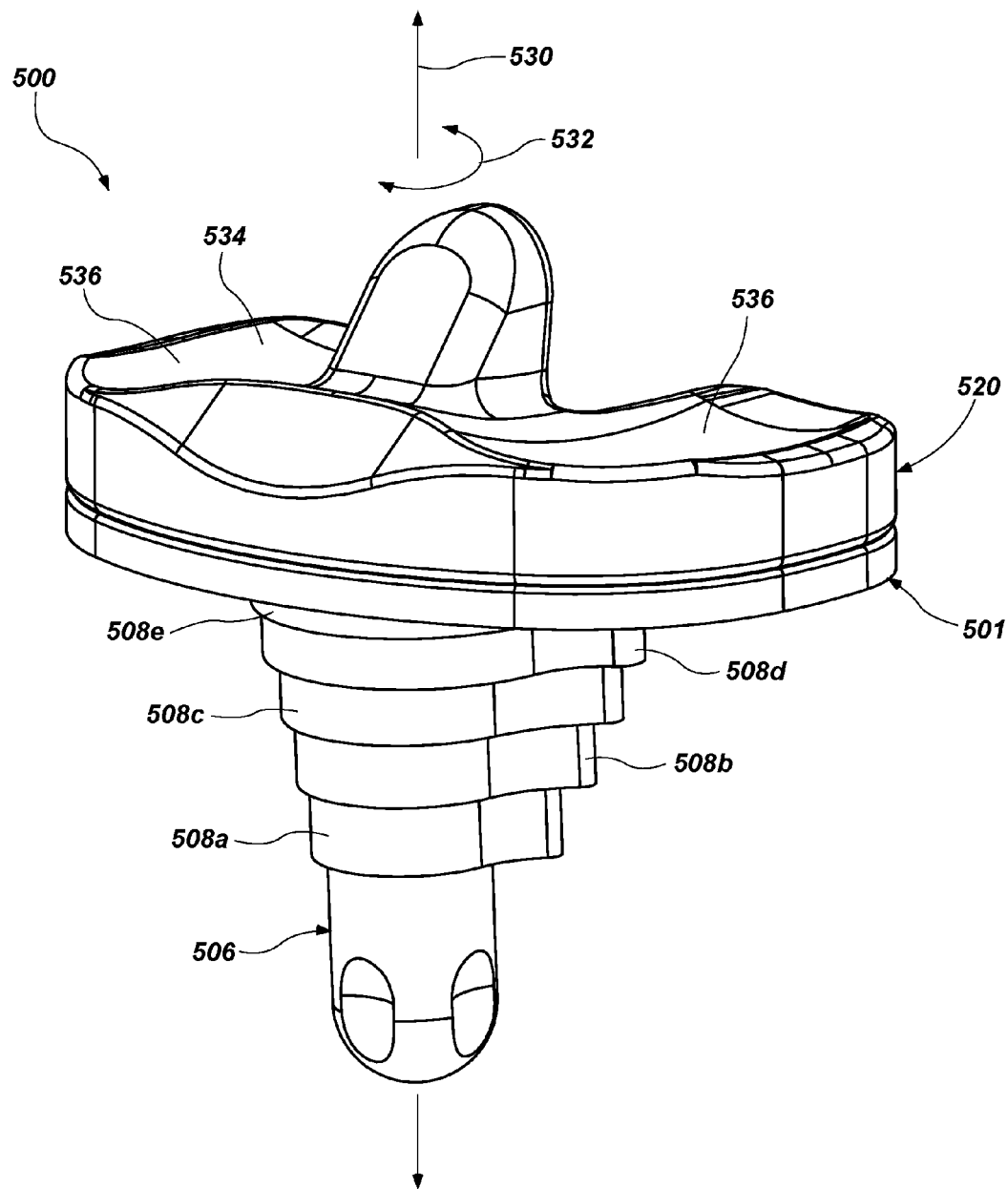
FIG. 16 is an unexploded, perspective view of the cementless tibial component and tibial bearing insert shown in FIG. 15.

In an embodiment, the superior surface 503 may include a stem cavity 510 for receiving a stem 522 extending from an inferior surface 524 of the tibial bearing insert 520. In particular, a rim 526 of the stem cavity 510 may form a tapered seat for receiving a tapered portion 528 of the stem 522. Both the superior surface 503 of the tibial component 501 and the inferior surface 524 of the tibial bearing insert 520 may be substantially planar such that the tibial bearing insert 520 may rotate with respect to the tibial component 501 about the axis 530 as shown by the arrows marked with the reference numeral 532 in FIG. 16. In particular, the stem 522 of the tibial bearing insert 520 may rotate within the cavity 510 of the tibial component 501.

In an embodiment, a superior surface 534 of the tibial bearing insert 520 may have one or more condylar regions 536 that are adapted to receive, and articulate with, complementary condyles of a femoral implant (not shown) as known to those having ordinary skill in the art.

First Exemplary Embodiment

A tibial implant comprising:
a tibial tray comprising an upper surface and a lower surface, an anterior side, a posterior side, a medial side, and a lateral side;
a tibial stem comprising a shaft and a plurality of protruding steps extending outwardly from the shaft;
wherein the tibial stem is formed in a unitary manner with respect to the tibial tray;
wherein the tibial stem extends in a distal direction from the lower surface of the tibial tray, such that the tibial implant is a monoblock tibial implant;
wherein each of the plurality of protruding steps is progressively and successively wider in the medial-lateral direction than the protruding step immediately beneath itself from the distal most protruding step to the proximal most protruding step.

Second Exemplary Embodiment

A tibial implant comprising:
a tibial tray comprising an upper surface and a lower surface, an anterior side, a posterior side, a medial side, and a lateral side, wherein the tibial tray comprises a tray width that between the medial side and the lateral side;
a tibial stem comprising a shaft and a plurality of protruding steps extending outwardly from the shaft;
wherein the tibial stem is formed in a unitary manner with respect to the tibial tray;
wherein the tibial stem extends in a distal direction from the lower surface of the tibial tray, such that the tibial implant is a monoblock tibial implant;
wherein each of the plurality of protruding steps comprises a step width defined as a distance that is less than, and formed between, the medial side and the lateral side of the tibial tray;
wherein a ratio between the tray width and the step width is between a range of about 1:0.75 and about 1:0.2.

The second exemplary embodiment disclosed above, wherein the stem width of each successive step as measured from the distal end of the stem to the proximal end of the stem increases.

The second exemplary embodiment disclosed above, wherein a ratio between the tray width and the step width of a distal most step is between a range of about 1:0.25 to about 1:0.35 and wherein a ratio between the tray width and the step width of a proximal most step is between a range of about 1:0.65 to about 1:0.55.

Third Exemplary Embodiment

A tibial implant comprising:
a tibial tray comprising an upper surface and a lower surface, an anterior side, a posterior side, a medial side, and a lateral side;
a tibial stem comprising a shaft and a plurality of protruding steps extending outwardly from the shaft;
wherein the tibial stem is formed in a unitary manner with respect to the tibial tray;
wherein the tibial stem extends in a distal direction from the lower surface of the tibial tray, such that the tibial implant is a monoblock tibial implant;
wherein each of the plurality of protruding steps comprises a thickness defined as a distance running the proximal to distal direction;
wherein the tibial tray comprises a sidewall that defines a perimeter of the top surface, wherein the sidewall comprises a height;
wherein a ratio between the thickness of at least one of the plurality of protruding steps to the height of the sidewall of the tibial tray is between a range of about 0.5:1 to about 1:1.

Fourth Exemplary Embodiment

A tibial implant comprising:
a tibial tray comprising an upper surface and a lower surface, an anterior side, a posterior side, a medial side, and a lateral side;
a tibial stem comprising a shaft and a plurality of protruding steps extending outwardly from the shaft;
wherein the tibial stem is formed in a unitary manner with respect to the tibial tray;
wherein the tibial stem extends in a distal direction from the lower surface of the tibial tray, such that the tibial implant is a monoblock tibial implant;
wherein the tibial implant further comprises a total length that is measured from a terminal end of the tibial tray on one end and a terminal end of the tibial stem at the other end;
wherein the tibial stem comprises a stem length that is measured from the lower surface of the tibial tray to the terminal end of the tibial stem;
wherein a ratio between the total length of the tibial implant to the stem length of the tibial stem is between a range of about 1:0.75 to about 1:0.95.

Fifth Exemplary Embodiment

A tibial implant comprising:
a tibial tray comprising an upper surface and a lower surface, an anterior side, a posterior side, a medial side, and a lateral side;
a tibial stem comprising a shaft and a plurality of protruding steps extending outwardly from the shaft;
wherein the tibial stem is formed in a unitary manner with respect to the tibial tray;
wherein the tibial stem extends in a distal direction from the lower surface of the tibial tray, such that the tibial implant is a monoblock tibial implant;

wherein the tibial implant further comprises a total length that is measured from a terminal end of the tibial tray on one end and a terminal end of the tibial stem at the other end;

wherein the plurality of protruding steps are formed between the lower surface of the tibial tray and a distal end of the tibial stem, such that there is a total length of the plurality of protruding steps that is defined by a distal most terminal end of the protruding step that is positioned as the distal most protruding step and a proximal most terminal end of the protruding step that is positioned as the proximal most protruding step;

wherein a ratio between the total length of the tibial implant to the length of the plurality of protruding steps is between a range of about 1:0.15 to about 1:0.55.

The fifth exemplary embodiment disclosed above, wherein the tibial implant is a revision implant and the ratio between the total length of the tibial implant to the length of the plurality of protruding steps is between a range of about 1:0.15 to about 1:0.20.

The fifth exemplary embodiment disclosed above, wherein the tibial implant is a primary implant and the ratio between the total length of the tibial implant to the length of the plurality of protruding steps is between a range of about 1:0.45 to about 1:0.55.

Sixth Exemplary Embodiment

A revision tibial implant comprising:

a tibial tray comprising an upper surface and a lower surface, an anterior side, a posterior side, a medial side, and a lateral side;

a tibial stem comprising a proximal shaft, a distal shaft and a plurality of protruding steps extending outwardly from the proximal shaft, wherein the proximal shaft is joined to the distal shaft at a joint;

wherein the proximal shaft comprises a transverse cross-section comprising a center point and the distal shaft comprises a transverse cross-section comprising a center point, wherein the center point of the proximal shaft is offset and non-linear with respect to the center point of the distal shaft;

wherein the proximal shaft of the tibial stem is formed in a unitary manner with respect to the tibial tray;

wherein the proximal shaft of the tibial stem extends in a distal direction from the lower surface of the tibial tray, such that the proximal shaft and the tibial tray are formed as a single structure without interchangeable parts in a monoblock design;

wherein the tibial implant further comprises a total length that is measured from a terminal end of the tibial tray on one end and a terminal end of the distal shaft of the tibial stem at the other end;

wherein the distal shaft of the tibial stem comprises a stem length that is measured from a terminal end of the joint proximally to the terminal, distal end of the distal shaft distally;

wherein a ratio between the total length of the tibial implant to the stem length of the distal shaft is between a range of about 1:0.4 to about 1:0.6.

The sixth exemplary embodiment disclosed above, wherein the joint between the proximal shaft and the distal shaft comprises a one-hundred and eighty degree transition from a positive slope to a negative slope such that the joint transition creates the offset between the proximal shaft and the distal shaft.

Seventh Exemplary Embodiment

A tibial implant comprising:

a tibial tray comprising an upper surface and a lower surface, an anterior side, a posterior side, a medial side, and a lateral side;

a tibial stem comprising a shaft and a plurality of protruding steps extending outwardly from the shaft;

wherein the tibial stem is formed in a unitary manner with respect to the tibial tray;

wherein the tibial stem extends in a distal direction from the lower surface of the tibial tray, such that the tibial implant is a monoblock tibial implant;

wherein the tibial stem comprises a plurality of concave portions located on the distal most one-third of the tibial stem;

wherein each of the plurality of concave portions lies in a quadrant defined by intersecting two imaginary planes perpendicularly to each other to create individual quadrants;

wherein the concave portion comprises about ten percent to about thirty percent of total planar section of a portion of the tibial stem that is free from the protruding steps.

Eighth Exemplary Embodiment

A tibial implant comprising:

a tibial tray comprising an upper surface and a lower surface, an anterior side, a posterior side, a medial side, and a lateral side;

a tibial stem comprising a shaft and a plurality of protruding steps extending outwardly from the shaft;

wherein the tibial stem is formed in a unitary manner with respect to the tibial tray;

wherein the tibial stem extends in a distal direction from the lower surface of the tibial tray, such that the tibial implant is a monoblock tibial implant;

wherein the tibial stem comprises a plurality of concave portions located on the distal most one-third of the tibial stem;

wherein each of the plurality of concave portions lies in a quadrant defined by intersecting two imaginary planes perpendicularly to each other to create individual quadrants;

wherein the concave portion comprises about forty percent to about seventy percent of a perimeter section of the distal most $1/3$ of the tibial stem.

Ninth Exemplary Embodiment

A tibial implant comprising:

a tibial tray comprising an upper surface and a lower surface, an anterior side, a posterior side, a medial side, and a lateral side;

a tibial stem comprising a shaft and a plurality of protruding steps extending outwardly from the shaft;

wherein the plurality of protruding steps each have one lobe portion or two lobe portions.

After considering the disclosure above, the following are exemplary embodiments of the disclosure. It is to be understood that this method of disclosure is not to be interpreted as reflecting an intention that the disclosure requires more features than are expressly recited in each embodiment disclosed below. Rather, inventive aspects lie in less than all features of a single disclosed embodiment.

Those having ordinary skill in the relevant art will appreciate the advantages provide by the features of the disclosure. For example, it is a potential feature of the disclosure to provide a cementless tibial implant that may be either a primary or revision implant that may be fixed to the tibial bone without the use of cement in a cementless application. It is another potential feature to provide a cementless tibial implant having a stepped design. It is yet another potential feature of the disclosure to provide such a cementless tibial implant in a monoblock design. It is a potential feature of the disclosure to provide a cementless tibial implant that does not use screws. It will be appreciated that there are other potential features not identified in this paragraph that are also obtained from the structures and systems disclosed herein.

In the foregoing Detailed Description of the Disclosure, various features of the disclosure are grouped together in a single embodiment for the purpose of streamlining the disclosure. This method of disclosure is not to be interpreted as reflecting an intention that the disclosure requires more features than are expressly recited in each claim of the non-provisional application. Rather, inventive aspects lie in less than all features of a single foregoing disclosed embodiment.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements. Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A knee prosthesis comprising:
   a monoblock tibial component having a tibial tray and a stem extending downwardly from an inferior surface of the tibial tray; and
   a plurality of steps formed in the stem;
   wherein at least two of the plurality of steps each comprises a first lobe portion, positioned closer to a posterior side of the stem than an anterior side of the stem, and a first pair of concave portions;
   wherein each of the first lobe portions is interposed between the first pair of concave portions on the same step.

2. The knee prosthesis of claim 1, wherein each of the at least two of the plurality of steps further comprises a second lobe portion and a second pair of concave portions.

3. The knee prosthesis of claim 2, wherein each of the second lobe portions is interposed between the second pair of concave portions on the same step.

4. The knee prosthesis of claim 3, wherein each of the at least two of the plurality of steps further comprises a third lobe portion.

5. The knee prosthesis of claim 4, wherein each of the third lobe portions is interposed between one of the first pair of concave portions and one of the second pair of concave portions on the same step.

6. The knee prosthesis of claim 1, wherein the first lobe portions define a medial stem wing and the second lobe portions define a lateral stem wing.

7. The knee prosthesis of claim 1, wherein the tibial tray comprises a superior surface, and the knee prosthesis further comprises a tibial bearing insert removably installable onto the superior surface of the tibial tray.

8. The knee prosthesis of claim 7, wherein the tibial bearing insert comprises a stem.

9. The knee prosthesis of claim 1, wherein a majority of the plurality steps each comprises a first lobe portion and a first pair of concave portions.

10. The knee prosthesis of claim 1, wherein all of the plurality steps each comprises a first lobe portion and a first pair of concave portions.

11. The knee prosthesis of claim 1, wherein the first lobe has two opposing sides, wherein each of the two opposing sides are located closer to the posterior side of the stem than the anterior side of the stem.

12. The knee prosthesis of claim 1, wherein the pair of concave portions of at least two of the steps comprises opposing concave portions which are both closer to the posterior side of the stem than an anterior side of the stem.

13. A knee prosthesis comprising:
    a stemless tibial bearing insert having an inferior surface and a superior surface;
    a monoblock tibial component having a tibial tray and a stem;
    the tibial tray having a superior surface and an inferior surface;
    the stem extending downwardly from the inferior surface of the tibial tray; and
    a plurality of steps formed in the stem;
    wherein the superior surface of the tibial tray is configured and adapted to matingly engage the inferior surface of the stemless tibial bearing insert;
    wherein the superior surface of the tibial tray is devoid of a stem cavity; and
    wherein the stem comprises a first stepped wing portion positioned closer to a posterior side of the stem than an anterior side of the stem.

14. The knee prosthesis of claim 13, wherein the stem comprises a second stepped wing portion.

15. The knee prosthesis of claim 14, wherein each of the plurality of steps comprise a first lobe portion and a second lobe portion.

16. The knee prosthesis of claim 15, wherein each lobe has two opposing sides, wherein each of the two opposing sides are located closer to a posterior side of the stem than an anterior side of the stem.

17. The knee prosthesis of claim 15, wherein each of the first and second lobe portions is interposed between a pair of concave portions of the step.

18. The knee prosthesis of claim 17, wherein at least one of the pairs of concave portions of the step comprises opposing concave portions which are both closer to a posterior side of the stem than an anterior side of the stem.

19. The knee prosthesis of claim 13, wherein the stem comprises a stepped portion and a non-stepped portion.

20. The knee prosthesis of claim 13, further comprising a means for locking the tibial bearing insert to the monoblock tibial component.

21. The knee prosthesis of claim 20, wherein the means for locking comprises a wall extending upwardly from a perimeter of the superior surface of the tibial tray; and an inwardly extending lip disposed along a top of said wall.

22. A knee prosthesis comprising:
    a monoblock tibial component having a tibial tray and a stem extending downwardly from an inferior surface of the tibial tray;
    the stem comprising a first wing portion extending outwardly therefrom and positioned closer to a posterior side of the stem than an anterior side of the stem; and
    a plurality of steps formed in the first wing portion.

23. The knee prosthesis of claim 22, wherein each of the plurality of steps of the first wing portion comprises a lobe portion.

24. The knee prosthesis of claim 23, wherein the lobe has two opposing sides, wherein each of the two opposing sides are located closer to the posterior side of the stem than an anterior side of the stem.

25. The knee prosthesis of claim 23, wherein the lobe portions are each interposed between a pair of concave portions on the same step.

26. The knee prosthesis of claim 25, wherein the pair of concave portions of the step comprises opposing concave portions which are both closer to the posterior side of the stem than an anterior side of the stem.

27. The knee prosthesis of claim 22, wherein the stem further comprises a second wing portion extending outwardly therefrom; and a plurality of steps formed in the second wing portion.

28. The knee prosthesis of claim 27, wherein each of the plurality of steps of the first wing portion comprises a lobe portion; and wherein each of the plurality of steps of the second wing portion comprises a lobe portion.

29. The knee prosthesis of claim 28, wherein each of the lobe portions of the first wing portion and the second wing portion are interposed between a pair of concave portions.

30. The knee prosthesis of claim 22, wherein the stem comprises a stepped portion and a non-stepped portion.

31. The knee prosthesis of claim 22, further comprising a tibial bearing insert removably installable onto the tibial tray.

32. A knee prosthesis comprising:
- a stemless tibial bearing insert having a superior surface and an inferior surface;
- a tibial component having a tibial tray comprising a superior surface and an inferior surface, a medial side, and a lateral side;
- the tibial component further comprising a tibial stem;
- wherein the tibial tray and the tibial stem are of unitary construction; and
- a plurality of steps formed in the tibial stem;
- wherein each of the steps comprises a first lobe portion and a second lobe portion, wherein each of the first lobe portion and the second lobe portion are positioned closer to a posterior side of the stem than an anterior side of the stem;
- wherein each of the steps further comprises a first pair of concave portions and a second pair of concave portions;
- wherein the first lobe portion of each step is disposed between the first pair of concave portions on the same step;
- wherein the second lobe portion of each step is disposed between the second pair of concave portions on the same step;
- wherein the first lobe portions of the plurality of steps define a medial stem wing;
- wherein the second lobe portions of the plurality of steps define a lateral stem wing;
- wherein the superior surface of the tibial tray is substantially planar and devoid of a stem cavity;
- wherein the tibial stem is formed in a unitary manner with respect to the tibial tray;
- wherein the tibial stem extends in a distal direction from the inferior surface of the tibial tray;
- wherein the tibial implant further comprises a total length that is measured from a proximal end of the tibial tray and a distal end of the tibial stem;
- wherein the tibial stem comprises a stem length that is measured from the inferior surface of the tibial tray to the distal end of the tibial stem;
- wherein a ratio between the total length of the tibial implant to the stem length of the tibial stem is between a range of about 1:0.75 to about 1:0.95;
- wherein the tibial tray comprises a tray width defined as a length between its medial side and its lateral side;
- wherein each of the plurality of steps comprises a step width defined as a distance that is less than, and formed between, the medial side and the lateral side of the tibial tray;
- wherein a ratio between the tray width and the step widths is between a range of about 1:0.2 and about 1:0.75;
- wherein each of the plurality of steps comprises a thickness defined as a distance in a proximal to distal direction;
- wherein the tibial tray comprises a sidewall that defines a perimeter of the superior surface, wherein the sidewall comprises a height;
- wherein a ratio between the thickness of at least one of the plurality of steps to the height of the sidewall of the tibial tray is between a range of about 0.5:1 to about 1:1.

* * * * *